US012565655B2

(12) United States Patent
Thompson

(10) Patent No.: US 12,565,655 B2
(45) Date of Patent: Mar. 3, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 19/216,307

(22) Filed: May 22, 2025

(65) Prior Publication Data

US 2025/0333743 A1 Oct. 30, 2025

Related U.S. Application Data

(60) Continuation of application No. 18/932,316, filed on Oct. 30, 2024, now Pat. No. 12,486,508, which is a division of application No. 18/518,069, filed on Nov. 22, 2023.

(51) Int. Cl.
*C12N 15/113* (2010.01)
*C12N 15/86* (2006.01)

(52) U.S. Cl.
CPC .......... *C12N 15/1137* (2013.01); *C12N 15/86* (2013.01); *C12N 2310/141* (2013.01); *C12N 2750/14143* (2013.01); *C12Y 207/01* (2013.01)

(58) Field of Classification Search
CPC .............. C12N 15/86; C12N 2310/141; C12N 2750/14143
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 | 11/2021 | Minshull et al. | |
| 11,530,423 B1 | 12/2022 | Thompson | |
| 11,873,505 B2 | 1/2024 | Thompson | |
| 12,018,274 B2 | 6/2024 | Thompson | |
| 12,134,770 B1* | 11/2024 | Thompson | C12N 15/86 |
| 12,195,747 B1* | 1/2025 | Thompson | C12N 15/111 |
| 12,281,309 B1* | 4/2025 | Thompson | C12N 15/86 |
| 2020/0362344 A1 | 11/2020 | Minshull et al. | |
| 2024/0026377 A1 | 1/2024 | Thompson | |

FOREIGN PATENT DOCUMENTS

CA 2721333 A1 10/2009

OTHER PUBLICATIONS

Kenji and Mizukami < star-protocols.cell.com/protocols/3185 >, Dec. 15, 2023, 17 pages, accessed on Sep. 9, 20225 (Year: 2023).*
Lundstrom K., Viruses. Mar. 7, 2023;15(3):698 (Year: 2023).*
FLT3 Sequence Genbank revision history Nov. 2023 , 14 pages. Retrieved from the United States NCBI webpage on the internet <https://www.ncbi.nlm.nih.gov> [retrieved on Feb. 11, 2025]. (Year: 2023).*
Wallace JA et al., Blood, Apr. 21, 2017;129(23):3074-3086 (Year: 2017).*
Ying et al. 2008. Mol. Biotechnol. 38:257-268 (Year: 2008).*
Lam et al. 2015. Molec. Ther. Nuc. Ac. 4:e252 (Year: 2015).*
Bottoni et al. "Targeting BTK through microRNA in chronic lymphocytic leukemia." Blood, The Journal of the American Society of Hematology 128.26 (2016): 3101-3112.
Christensen et al. "Recombinant adeno-associated virus-mediated microRNA delivery into the postnatal mouse brain reveals a role for miR-134 in dendritogenesis in vivo." Frontiers in neural circuits 3 (2010): 848.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Brutons Tyrosine Kinase Genbank Sequence (2023).
GenBank EGFR Sequence (2023).
Nature (2010. Gene Expression. Scitable. Available online at Nature. com) <https://www.nature.com/scitable/topicpage/gene-expression-14121669> (2010).
Tritschler et al. "Concepts and limitations for learning developmental trajectories from single cell genomics." Development 146.12 (2019): dev170506.
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for SEQ ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).

(Continued)

*Primary Examiner* — Ram R Shukla
*Assistant Examiner* — Shabana S Meyering
(74) *Attorney, Agent, or Firm* — Gowling WLG (Canada) LLP

(57) ABSTRACT

The embodiments of the present disclosure relate to decreasing the bioavailability of Fms-like tyrosine kinase 3 (FLT3) by providing a composition that comprises a recombinant plasmid with one or more sequences of miRNA. When the recombinant plasmid interacts with a target cell, it causes the target cell to upregulate production of the miRNA, which then decreases the bioavailability of FLT3.

2 Claims, No Drawings

Specification includes a Sequence Listing.

(56) References Cited

OTHER PUBLICATIONS

NCBI Nucleotide Sequence for PARP, search performed Dec. 26, 2024 (2024).

GenBank FLT3 Sequence (2024).

O'Brien et al. "Overview of microRNA biogenesis, mechanisms of actions, and circulation." Frontiers in endocrinology 9 (2018): 402.

Gorski et al. "RNA-based recognition and targeting: sowing the seeds of specificity." Nature Reviews Molecular Cell Biology 18.4 (2017): 215-228.

GenBank EGF Sequence (2023).

Kondratov et al. "Direct head-to-head evaluation of recombinant adeno-associated viral vectors manufactured in human versus insect cells." Molecular Therapy 25.12 (2017): 2661-2675.

Wang et al. "Adeno-associated virus vector as a platform for gene therapy delivery." Nature reviews Drug discovery 18.5 (2019): 358-378.

Pagliuca (et al. 2013. Analysis of the combined action of miR-143 and miR-145 on oncogenic pathways in colorectal cancer cells reveals a coordinate program of gene repression. Oncogene 32:4806-4813) (Year: 2013).

Fattore (et al. 2016. miR-579-3p controls melanoma progression and resistance to target therapy. PNAS 113 [34]:E5005-E5013) ( Year: 2016).

Origene (2024. Product datasheet for SC207797 B Raf [BRAF] [NM_004333] Human 3' UTR Clone. Rockville, MD: Origene) (Year:2024).

NCBI (*Homo sapiens* B-Raf proto-oncogene, serine/threonine kinase [BRAF], transcript variants 1-2, 4-14, mRNA: [see reference for NM number]. Available online at NCBI.nlm.nih.gov. Accessed on May 16, 2025 (Year: 2025).

MiRbase (2025. "miR-143" and "miR-145", and "miR-579-3p". Available online at miRbase.org. Accessed on May 16, 2025) (Year: 2025).

*Homo sapiens* VEGF, mRNA, NCBI Reference Sequence, version Oct. 2023, 9 pages, retrieved from the internet Jul. 2, 2025 (Year: 2023).

Zhang et al. Drug Design, Development and Therapy, Published Feb. 22, 2021, pp. 721-733. (Year: 2021).

* cited by examiner

SEQUENCE LISTING

```
Sequence total quantity: 17
SEQ ID NO: 1           moltype = DNA  length = 5883
FEATURE                Location/Qualifiers
source                 1..5883
                       mol_type = other DNA
                       organism = synthetic construct
SEQUENCE: 1
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttat   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacggttaat  1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg ctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaacccttat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaattat cagctagaac ggttgaatat  1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
```

```
cgcttacaga caagctgtga ccgtctccgg gagctgcatg tgtcagaggt tttcaccgtc 2460
atcaccgaaa cgcgcgagac gaaagggcct cgtgatacgc ctatttttat aggttaatgt 2520
catgataata atggtttctt agacgtcagg tggcactttt cggggaaatg tgcgcggaac 2580
ccctatttgt ttattttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
tttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttaacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagatacctta cagcgtgagc tatgagaaag cgccacgctt cccgaaggga gaaaggcgga 4140
caggtatccg gtaagcggca gggtcggaac aggagagcgc acgagggagc ttccagggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggcctttttt 4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctcccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca tgctctagga cattgattat tgactagtgg 4740
agttccgcgt tacataactt acggtaaatg gcccgcctgg ctgaccgccc aacgacccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgccccct attgacgtca atgacggtaa atggcccgcc tggcattatg 4980
cccagtacat gaccttatgg gactttccta cttggcagta catctacgta ttagtcatcg 5040
ctattaccat ggtcgaggtg agccccacgt tctgcttcac tctccccatc tcccccccct 5100
ccccacccc aattttgtat ttatttattt tttaattatt ttgtgtcagcg atgggggcgg 5160
ggggggggg gggcgcgcgc caggcggggc ggggcggggc gaggggcgggg gcggggcgag 5220
gcggagaggt gcggcggcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgcccgtgc cccgctccgc cgccgcctcg cgccgcccgc cccggctctg 5400
actgaccgcg ttactaaaac aggtaagtcc ggcctccgcg ccggttttg gcgcctcccg 5460
cgggcgcccc cctcctcacg gcgagcgctg ccacgtcaga cgaagggcgc agcgagcgtc 5520
ctgatccttc cgcccggacg ctcaggacag cggcccgctg ctcataagac tcggccttag 5580
aaccccagta tcagcagaag gacatttttag gacgggactt gggtgactct agggcactgg 5640
ttttctttcc agagagcgga acaggcgagg aaaagtagtc ccttctcggc gattctgcgg 5700
agggatctcc gtggggcggt gaacgccgat gatgcctcta ctaaccatgt tcatgttttc 5760
ttttttttttc tacaggtcct gggtgacgaa caggagtaccg ccaccatggc caccggctct 5820
cgcacaagcc tgctgctggc tttcggactg ctgtgcctgc cttggctcca ggagggctcc 5880
gcc                                                                 5883
```

```
SEQ ID NO: 2          moltype = DNA  length = 456
FEATURE               Location/Qualifiers
source                1..456
                      mol_type = other DNA
                      organism = synthetic construct
SEQUENCE: 2
gctagcatcg ataccgtcgc tatgtgctgg aggcttgctg aaggctgtat gctgtaaggt 60
ggttatggga gaatgccgtt ttggcctctg actacggca ttctcctaac caccttacag 120
gacacaaggc ctgttactag cactcacatg gaacaaatgt cctctagcct ggaggcttgc 180
tgaaggctgt atgctgttga gtttcgcatt cttgttgccg ttttggcctc tgactgacgg 240
caacaagagc gaaactcaac aggacacaag gcctgttact agcactcaca tggaacaaat 300
ggcctctagc ctgaggctt gctgaaggct gtatgctgtc tatcctttca agctagtcac 360
cgttttggc tctgactgac ggtgactagc gaaaggatag acaggacaca aggcctgtta 420
ctagcactca catggaacaa atggcctctc tagaat 456
```

```
SEQ ID NO: 3          moltype = DNA  length = 456
FEATURE               Location/Qualifiers
source                1..456
                      mol_type = other DNA
```

```
                        organism = synthetic construct
SEQUENCE: 3
gctagcatcg ataccgtcgc tatgtgctgg aggcttgctg aaggctgtat gctgaagtta    60
gcatgtgtcc cagaaccgtt ttggcctctg actgacggtt ctgggacatg ctaacttcag   120
gacacaaggc ctgttactag cactcacatg gaacaaatgg cctctagcct ggaggcttgc   180
tgaaggctgt atgctgagaa gaaaggtatc ccaattgccg ttttggcctc tgactgacgg   240
caattgggac ctttcttctc aggacacaag gcctgttact agcactcaca tggaacaaat   300
ggcctctagc ctggaggctt gctgaaggct gtatgctgta gtgtttccaa atactgcttg   360
cgtttttggc tctgactgac gcaagcgta  tggaaacact acaggacaca aggcctgtta   420
ctagcactca catggaacaa atggcctctc tagaat                            456

SEQ ID NO: 4            moltype = DNA   length = 456
FEATURE                 Location/Qualifiers
source                  1..456
                        mol_type = other DNA
                        organism = synthetic construct
SEQUENCE: 4
gctagcatcg ataccgtcgc tatgtgctgg aggcttgctg aaggctgtat gctgtctgac    60
agtgatgtca tcctttcgtt ttggcctctg actgacgaaa ggatgatcac tgtcagacag   120
gacacaaggc ctgttactag cactcacatg gaacaaatgg cctctagcct ggaggcttgc   180
tgaaggctgt atgctgattt aggtcagatg gaaactcgcg ttttggcctc tgactgacgc   240
gagtttccct gacctaaatc aggacacaag gcctgttact agcactcaca tggaacaaat   300
ggcctctagc ctggaggctt gctgaaggct gtatgctgag tgtatgctta acgtggactt   360
cgtttttggc tctgactgac gaagtccacg aagcatacac tcaggacaca aggcctgtta   420
ctagcactca catggaacaa atggcctctc tagaat                            456

SEQ ID NO: 5            moltype = DNA   length = 456
FEATURE                 Location/Qualifiers
source                  1..456
                        mol_type = other DNA
                        organism = synthetic construct
SEQUENCE: 5
gctagcatcg ataccgtcgc tatgtgctgg aggcttgctg aaggctgtat gctgatactt    60
cagcctgaat cgtgaccgtt ttggcctctg actgacgagtc acgattggct gaagtatcag   120
gacacaaggc ctgttactag cactcacatg gaacaaatgg cctctagcct ggaggcttgc   180
tgaaggctgt atgctgactt cactcatatt gttccactcg ttttggcctc tgactgacga   240
gtggaacaat gagtgaagtc aggacacaag gcctgttact agcactcaca tggaacaaat   300
ggcctctagc ctggaggctt gctgaaggct gtatgctgta tattctacaa atcaccaggg   360
cgtttttggc tctgactgac gccctggtga tgtagaatat acaggacaca aggcctgtta   420
ctagcactca catggaacaa atggcctctc tagaat                            456

SEQ ID NO: 6            moltype = DNA   length = 456
FEATURE                 Location/Qualifiers
source                  1..456
                        mol_type = other DNA
                        organism = synthetic construct
SEQUENCE: 6
gctagcatcg ataccgtcgc tatgtgctgg aggcttgctg aaggctgtat gctgtataag    60
tccagtgaga agaaggcgtt ttggcctctg actgacgcct tcttctctgg acttatacag   120
gacacaaggc ctgttactag cactcacatg gaacaaatgg cctctagcct ggaggcttgc   180
tgaaggctgt atgctgctat catcaaatga gctgctgcgt tttggcctct gactgacgca   240
gcagctcttg atgatagtca ggacacaagg cctgttacta gcactcacat ggaacaaatg   300
gcctctagcc tggaggcttg ctgaaggctg tatgctgaag actgctggaa attctatggc   360
tgtttttggc tctgactgac gaccatagaa tccagcagtc tcaggacaca aggcctgtta   420
ctagcactca catggaacaa atggcctctc tagaat                            456

SEQ ID NO: 7            moltype = DNA   length = 457
FEATURE                 Location/Qualifiers
source                  1..457
                        mol_type = other DNA
                        organism = synthetic construct
SEQUENCE: 7
gctagcatcg ataccgtcgc tatgtgctgg aggcttgctg aaggctgtag gctgattagc    60
actggtgatt tccggctgtt ttggcctctg actgacgacc ggaaatccag tgctaatcag   120
gacacaaggc ctgttactag cactcacatg gaacaaatgg cctctagcct ggaggcttgc   180
tgaaggctgt atgctgattg agtttcgcat tcttgttgcc gttttggcct ctgactgacg   240
gcaacaagag cgaaactcaa caggacacaa ggcctgttac tagcactcac atggaacaaa   300
tggcctctag cctggaggct tgctgaaggc tgtatgctga ttgatcaggc aaacatagtc   360
ccgtttttggc ctctgactga cgggactatg tgcctgatca atcaggacac aaggcctgtt   420
actagcactc acatggaaca aatggcctct ctagaat                           457

SEQ ID NO: 8            moltype = DNA   length = 456
FEATURE                 Location/Qualifiers
source                  1..456
                        mol_type = other DNA
                        organism = synthetic construct
SEQUENCE: 8
gctagcatcg ataccgtcgc tatgtgctgg aggcttgctg aaggctgtat gctgtctgat    60
cgtggtgtta tttgggcgtt ttggcctctg actgacgccc aaataaccac gatcagacag   120
```

```
gacacaaggc ctgttactag cactcacatg gaacaaatgg cctctagcct ggaggcttgc   180
tgaaggctgt atgctgttga gtttcgcatt cttgttgccg ttttggcctc tgactgacgg   240
caacaagagc gaaactcaac aggacacaag gcctgttact agcactcaca tggaacaaat   300
ggcctctagc ctggaggctt gctgaaggct gtatgctgta tcctcttata actcagcctc   360
cgttttggcc tctgactgac ggaggctgag ataagaggat acaggacaca aggcctgtta   420
ctagcactca catggaacaa atggcctctc tagaat                              456

SEQ ID NO: 9           moltype = DNA   length = 456
FEATURE                Location/Qualifiers
source                 1..456
                       mol_type = other DNA
                       organism = synthetic construct
SEQUENCE: 9
gctagcatcg ataccgtcgc tatgtgctgg aggcttgctg aaggctgtat gctgtcgtac   60
tgacttgtag gtatgccgtt ttggcctctg actgacggca tacctaagtc agtacgtcag   120
gacacaaggc ctgttactag cactcacatg gaacaaatgg cctctagcct ggaggcttgc   180
tgaaggctgt atgctgactc ctaatcaata gcttccaccg ttttggcctc tgactgacgg   240
tggaagcttg attaggagtc aggacacaag gcctgttact agcactcaca tggaacaaat   300
ggcctctagc ctggaggctt gctgaaggct gtatgctgaa tatgccttta agctttgctg   360
cgttttggcc tctgactgac gcagcaaagc aaaggcatat tcaggacaca aggcctgtta   420
ctagcactca catggaacaa atggcctctc tagaat                              456

SEQ ID NO: 10          moltype = DNA   length = 6339
FEATURE                Location/Qualifiers
source                 1..6339
                       mol_type = other DNA
                       organism = synthetic construct
SEQUENCE: 10
aatcaacctc tggattacaa aatttgtgaa agattgactg gtattcttaa ctatgttgct   60
cctttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt cccctcct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccggggg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa acggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcgcgc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta caggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga agctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcacttt cggggaaatg tgcgcggaac   2580
ccctatttgt ttatttttct aaatacattc aaatatgtat ccgctcatga caataacc    2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg gcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
```

-continued

```
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acgggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatcccctt aacgtgagtt   3660
ttcgttccac tgagcgtcag acccccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctga   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg ggggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttttt   4320
acggttcctg gccttttgct ggccttttgc tcacatgttc tttcctgcgt tatccccctga   4380
ttctgtggat aaccgtatta ccgcctttga gtgagctgat accgctcgcc gcagccgaac   4440
gaccgagcgc agcgagtcag tgagcgagga gcggaagag cgcccaatac gcaaaccgcc   4500
tctccccgcg cgttggccga ttcattaatg cagcagctgc gcgctcgctc gctcactgag   4560
gccgcgccgg caaagcccgg gcgtcgggcg acctttggtc gcccggcctc agtgagcgga   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgaccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aattttgtat ttatttattt tttaattatt ttgtgcagcg atgggggcgg   5160
gggggggggg gggcgcgcgc caggcggggc ggggcgggggc gagggccggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacatttttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttttc tacaggtcct gggtgacgaa cagggtaccg ccaccatggc caccggctct   5820
cgcacaagcc tgctgctggc tttcggactg ctgtgcctga cttggctccg agaagcatcc   5880
gccgctagca tcgataccgt cgctatgtgc tggaggcttg ctgaaggctg tatgctgtaa   5940
ggtggttatg ggagaatgcc gttttggcct ctgactgacg gcattctcct aaccaccttga   6000
caggacacaa ggcctgttac tagcactcac atggaacaaa tggcctctag cctggaggct   6060
tgctgaaggc tgtatgctgt tgagtttcgc attcttgttg ccgttttgc ctctgactga   6120
cggcaacaag agcgaaactc aacaggacac aaggcctgtt actagcactc acatggaaca   6180
aatggcctct agcctggagg cttgctgaag gctgtatgct gtctatcctt tcaagctagt   6240
caccgttttg gcctctgact gacggtgact agcgaaagga tagacaggac acaaggcctg   6300
ttactagcac tcacatggaa caaatggcct ctctagaat                         6339
```

```
SEQ ID NO: 11        moltype = DNA   length = 6339
FEATURE              Location/Qualifiers
source               1..6339
                     mol_type = other DNA
                     organism = synthetic construct
SEQUENCE: 11
aatcaacctc tggattacaa aatttgtgaa agattgactg gtattcttaa ctatgttgct   60
cctttacgc tatgtggata cgctgcttta atgcctttg atcatgctat tgcttccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtcctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttttt ttcactgcat tctagttgtg gtttgtccaa   720
actcatcaat gtatcttatc atgtctggat ctcgacctcg actagagcat ggctacgtag   780
ataagtagca tggcgggtta tcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
```

```
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggcg taccgttcct gtctaaaatc cctttaatcg gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tcctttctcg ccacgttcgc    1440
cggctttccc cgtcaagctc taaatcgggg gctcccttta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaaccctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaattttta tccttgcgtt    2100
gaaataaagg cttctcccgc aaaagtatta caggtcata atgttttttgg tacaaccgat    2160
ttagctttat gctctgaggc tttattgctt aattttgcta attctttgcc ttgcctgtat    2220
gatttattgg atgttggaat tcctgatgcg gtattttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctatttttat aggttaatgt    2520
catgataata atggtttctt agacgtcagg tggcacttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt cccttttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
ttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat taatagactg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagatACCta cagcgtgagc tatgagaaag cgccacgctt cccgaaggga gaaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttt    4320
acggttcctg gccttttgct ggccttttgc tcacatgttc tttcctgcgt tatccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagccggg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgacccc    4800
gcccattgac gtcaataatg acgtatgttc ccatagtaac acgataaggg aactttccat    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tcccccccct    5100
ccccaccccc aattttgtat ttatttattt ttaattatt ttgtgcagcg atgggggcgg    5160
gggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ggcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgttttc    5760
```

-continued

```
ttttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgaag   5940
ttagcatgtg tcccagaacc gttttggcct ctgactgacg gttctgggac atgctaactt   6000
caggacacaa ggcctgttac tagcactcac atggaacaaa tggcctctag cctggaggct   6060
tgctgaaggc tgtatgctga aagaaaggt atcccaattg ccgttttggc ctctgactga   6120
cggcaattgg gacctttctt ctcaggacac aaggcctgtt actagcactc acatggaaca   6180
aatggcctct agcctggagg cttgctgaag gctgtatgct gtagtgtttc caaatactgc   6240
ttgcgttttg gcctctgact gacgcaagca gtatggaaac actacaggac acaaggcctg   6300
ttactagcac tcacatggaa caaatggcct ctctagaat                           6339
```

SEQ ID NO: 12    moltype = DNA length = 6339
FEATURE        Location/Qualifiers
source         1..6339
            mol_type = other DNA
            organism = synthetic construct

SEQUENCE: 12

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccgggca ctttcgcttt cccctcccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcgcgcct gctgccggct cggcgccct taagcttatc   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttag ggttccgat ttagtgcttt   1500
acggcacctc gaccccaaaa aacttgatta gggtgatggt tcacgtagtg ggccatcgcc   1560
ctgatagacg gttttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggctttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cactttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
```

-continued

```
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccagggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctga gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg   5160
ggggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtgggcggt gaacgccgat gatgcctcta ctaaccatgt tcatgttttc   5760
tttttttttc tacaggtcct gggtgacgaa cagggtaccg ccaccatgac caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtct   5940
gacagtgatg tcatcctttc gttttggcct ctgactgacg aaaggatgat cactgtcaga   6000
caggacacaa ggcctgttac tagcactcac atggaacaaa tggcctctag cctggaggct   6060
tgctgaaggc tgtatgctga tttaggtcag atggaaactc gcgttttggc ctctgactga   6120
cgcgagtttc cctgacctaa atcaggacac aaggcctgtt actagcactc acatggaaca   6180
aatggcctct agcctggagg cttgctgaag gctgtatgct gagtgtatgc ttaacgtgga   6240
cttcgttttg gcctctgact gacgaagtcc acgaagcata cactcaggac acaaggcctg   6300
ttactagcac tcacatggaa caaatggcct ctctagaat   6339
```

SEQ ID NO: 13          moltype = DNA   length = 6339
FEATURE                Location/Qualifiers
source                 1..6339
                       mol_type = other DNA
                       organism = synthetic construct
SEQUENCE: 13

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg agagagctag actacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca caaggacgga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcta taccgttcct gtctaaaatc ccttttaatcg gcctcctgtt tagctcccgc   1260
tctgattcta acgaggaaag cacgttatac gtgctcgtca aagcaaccat agtacgcgc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gggttccgat ttagtgcttt   1500
acggcacctc gaccccaaaa aacttgatta gggtgatggt tcacgtagtg gccatcgcc   1560
ctgatagacg gtttttcgcc ctttgacgtt ggagtccacg ttctttaata gtggactctt   1620
gttccaaact ggaacaacac tcaacccctat ctcggtctat tcttttgatt tataagggat   1680
```

```
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaatttta tccttgcgtt    2100
gaaataaagg cttctcccgc aaaagtatta cagggtcata atgttttgg tacaaccgat    2160
ttagctttat gctctgaggc tttattgctt aattttgcta attctttgcc ttgcctgtat    2220
gatttattgg atgttggaat tcctgatgcg gtatttttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctattttttat aggttaatgt    2520
catgataata atggtttctt agacgtcagg tggcactttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt cccttttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
tttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat taatagactg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagataccta cagcgtgagc tatgagaaag cgccacgctt cccgaaggga aaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtag    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tcccccccct    5100
ccccaccccc aattttgtat ttatttatttt tttaattatt ttgtgcagcg atgggggcgg    5160
gggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgttttc    5760
ttttttttttc tacaggtcct gggtgacgaa cagggtaccg ccaccatgtc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgata    5940
cttcagcctg aatcgtgacc gtttttggcct ctgactgacg gtcacgattg ctgaagtat    6000
caggacacaa ggcctgttac tagcactcac atggaacaaa tggcctctag cctggaggct    6060
tgctgaaggc tgtatgctga cttcactcat attgttccac tcgttttggc ctctgactga    6120
cgagtcggaac aatgagtgaa gtcaggacac aaggcctgtt actagcactc acatggaaca    6180
aatgccctct agcctggagg cttgctgaag gctgtatgct gtatattcta caaatcacca    6240
gggcgttttg gcctctgact gacgccctgg tgatgtagaa tatacaggac acaaggcctg    6300
ttactagcac tcacatggaa caaatggcct ctctagaat                            6339
```

-continued

```
SEQ ID NO: 14          moltype = DNA   length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct    60
cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt cccctccct    300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc cttttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcggggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc  1020
gttgcaatgg ctggcggtaa tattgttctg gatattacca gcaaggccga tagtttgagt  1080
tcttctactc aggcaagtga tgttattact aatcaaagaa gtattgcgac aacgttaat   1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg ggccatcgcc  1560
ctgatagacg gtttttcgcc ctttgacgtt ggagtccacg ttctttaata gtggactctt  1620
gttccaaact ggaacaacac tcaaccctat ctcggtctat tcttttgatt tataagggat  1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaatttat cagctagaac ggttgaatat  1980
catattgatg gtgatttgac tgtctccggc ctttctcacc cgtttgaatc tttacctaca  2040
cattactcag gcattgcatt aaaaatatat gagggttcta aaaatttta tccttgcgtt  2100
gaaataaagg cttctcccgc aaaagtatta cagggtcata atgtttttgg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctatttttat aggttaatgt  2520
catgataata atggtttctt agacgtcagg tggcactttt cggggaaatg tgcgcggaac  2580
ccctatttgt ttatttttct aaatacattc aaatatgtat ccgctcatga gacaataacc  2640
ctgataaatg cttcaataat attgaaaaag gaagagtatg agtattcaac atttccgtat  2700
cgcccttatt ccctttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagatacctac agcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
```

```
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactgggg gttccttgta gttaatgatt   4680
aacccgccat gctacttatc tacgtagcca tgctctagga cattgattat tgactagttg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaaatg ggtggagtat ttacggtaaa ctgcccactt ggcagtacat caagtgtatc   4920
atatgccaag tacgcccect attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccccc aattttgtat ttatttattt tttaattatt ttgtgcagcg atgggggcgg   5160
gggggggggc gggcgcgcgc caggcggggc ggggcgggggc gaggggcggg gcgggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggtttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacattttag gacgggactt gggtgactct agggcactgg   5640
ttttcttttcc agagacggga acaggcgagg aaaagtagtc ccttctcggc gattctgcgg   5700
agggatctcc gtgggggcggt gaacgccgat gatgcctcta ctaaccatgt tcatgttttc   5760
ttttttttttt tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtat   5940
aagtccagtg agaagaaggc gttttggcct ctgactgacg ccttcttctc tggacttata   6000
caggacacaa ggcctgttac tagcactcac atggaacaaa tggcctctag cctgaaggct   6060
tgctgaaggc tgtatgctgc tatcatcaaa tgagctgctg cgtttggcc tctgactgac   6120
gcagcagctc ttgatgatag tcaggacaca aggcctgtta ctagcactca catggaacaa   6180
atggcctcta gcctgaaggc ttgctgaagg ctgtatgctg aagactgctg gaaattctat   6240
ggctgttttg gcctctgact gacgaccata gaatccagca gtctcaggac acaaggcctg   6300
ttactagcac tcacatggaa caaatggcct ctctagaat                          6339
```

```
SEQ ID NO: 15            moltype = DNA   length = 6340
FEATURE                  Location/Qualifiers
source                   1..6340
                         mol_type = other DNA
                         organism = synthetic construct
SEQUENCE: 15
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccggggc accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tccttcctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggctttt tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
```

```
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt   2520
catgataata atgtttctt agacgtcagg tggcactttt cggggaaatg tgcgcggaac   2580
ccctatttgt ttattttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacct cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccacccc aattttgtat ttatttattt tttaattatt ttgtgcagcg atgggggcgg   5160
gggggggggg gggcgcgcgc caggcggggc ggggcggggc gaggggcggg gcggggcgag   5220
gcgggagagg gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgctgcc cttggctcca ggagggctcc   5880
gccgctagca tcgataccgt cgctatgtgc tggaggctgc tcgaaggctg tatgctgatt   5940
agcactggtg atttccggct gttttggcct ctgactgacg accggaaatc cagtgctaat   6000
caggacacaa ggcctgttac tagcactcac atggaacaaa tggcctctag cctggaggct   6060
tgctgaaggc tgtatgctga ttgagtttcg cattcttgtt gccgttttgg cctctgactg   6120
acggcaacaa gagcgaaact caacaggaca caaggcctct tactagcact cacatggaac   6180
aaatggcctc tagcctggag gcttgctgaa ggctgtatgc tgattgatca ggcaaacata   6240
gtcccgtttt ggcctctgac tgacgggact atgtgcctga tcaatcagga cacaaggcct   6300
gttactagca ctcacatgga acaaatggcc tctctagaat                         6340
```

SEQ ID NO: 16          moltype = DNA   length = 6339
FEATURE                Location/Qualifiers
source                 1..6339
                       mol_type = other DNA
                       organism = synthetic construct
SEQUENCE: 16
```
aatcaacctc tggattacaa aatttgtgaa agattgactg gtattcttaa ctatgttgct   60
cctttacgc tatgtggata cgctgcttta atgcctttgt atcatgctat tgcttccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
```

-continued

```
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctcccccgc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccggggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gttttcgccc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccgt gctacttatc tacgtagcca cattgattat tgactagtga   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacgtaa atggcccgcc tggcattatg   4980
cccagtacat gaccttatgg gactttccta cttggcagta catctacgta ttagtcatcg   5040
```

```
ctattaccat ggtcgaggtg agccccacgt tctgcttcac tctccccatc tcccccccct   5100
ccccaccccc aattttgtat ttatttattt tttaattatt ttgtgcagcg atgggggcgg   5160
gggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcgcg cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctc ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtct   5940
gatcgtggtg ttatttgggc gttttggcct ctgactgacg cccaaataac cacgatcaga   6000
caggacacaa ggcctgttac tagcactcac atggaacaaa tggcctctag cctggaggct   6060
tgctgaaggc tgtatgctgt tgagtttcgc attcttgttg ccgtttttgc ctctgactga   6120
cggcaacaag agcgaaactc aacaggacac aaggcctgtt actagcactc acatggaaca   6180
aatggcctct agcctggagg cttgctgaag gctgtatgct gtatcctctt ataactcagc   6240
ctccgttttg gcctctgact gacggaggct gagataagag gatacaggac acaaggcctg   6300
ttactagcac tcacatggaa caaatggcct ctctagaat                          6339
```

```
SEQ ID NO: 17           moltype = DNA  length = 6339
FEATURE                 Location/Qualifiers
source                  1..6339
                        mol_type = other DNA
                        organism = synthetic construct
SEQUENCE: 17
aatcaacctc tggattacaa aatttgtgaa agattgactg gtattcttaa ctatgttgct   60
cctttacgc tatgtggata cgctgcttta atgcctttgt atcatgctat tgcttcccgt    120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggtggggca ttgccaccac ctgtcagctc ctttccggga ctttcgcttt ccccctccct    300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta tcattaact acaaggaaact cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt  1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggct taccgttcct gtctaaaatc ccttttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttt ctgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcca aaaattttta tccttgcgtt   2100
gaaataaagg cttctcccgc aaaagtatta caggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataaccc    2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga  3000
```

-continued

```
aaagcatctt acggatggca tgacagtaag agaattatgc agtgctgcca taaccatgag  3060
tgataacact gcggccaact tacttctgac aacgatcgga ggaccgaagg agctaaccgc  3120
tttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg ggcggagcct atggaaaaac gccagcaacg cggccttttt  4320
acggttcctg gccttttgct ggccttttgc tcacatgttc tttcctgcgt tatcccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccccc  4800
gcccattgac gtcaataatg acgtatgttc ccatagtaac gccaataggg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccccc aattttgtat ttatttattt tttaattatt ttgtgcagcg atggggggcgg  5160
ggggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcggggcg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttaa  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtgggcggt gaacgccgat gatgcctcta ctaaccatgt tcatgttttc  5760
tttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgtcg  5940
tactgacttg taggtatgcc gttttggcct ctgactgacg gcataccaa gtcagtacgt  6000
caggacacaa ggcctgttac tagcactcac atggaacaaa tggcctctag cctggaggct  6060
tgctgaaggc tgtatgctga ctcctaatca atagcttcca ccgttttggc ctctgactga  6120
cggtggaagc ttgattagga gtcaggacac aaggcctgtt actagcactc acatggaaca  6180
aatgcctct agcctggagg cttgctgaag gctgtatgct gaatatgcct ttaagctttg  6240
ctgcgttttg gcctctgact gacgcagcaa agcaaaggca tattcaggac acaaggcctg  6300
ttactagcac tcacatggaa caaatggcct ctctagaat                         6339
```

COMPOSITION FOR REGULATING PRODUCTION OF INTERFERING RIBONUCLEIC ACID

CROSS REFERENCE TO RELATED APPLICATION

The present application is a continuation of U.S. patent application Ser. No. 18/932,316 filed Oct. 30, 2024, entitled "COMPOSITION FOR REGULATING PRODUCTION OF INTERFERING RIBONUCLEIC ACID" currently pending, which is a division of U.S. patent application Ser. No. 18/518,069 filed Nov. 22, 2023, entitled "COMPOSITION FOR REGULATING PRODUCTION OF INTERFERING RIBONUCLEIC ACID" currently pending, the entirety of which is incorporated herein by reference.

SEQUENCE LISTING

This application contains a Sequence Listing electronically submitted via Patent Center to the United States Patent and Trademark Office as an XML Document file entitled "A8149358US—Sequence Listing.xml" created on 2023 Nov. 17 and having a size of 75,546 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA that will suppress over-expression or mis-expression of kinases.

BACKGROUND

Bioactive molecules, including kinases, are necessary for the homeostatic control of biological systems.

When bioactive molecules are over-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro interfering ribonucleic acid (miRNA). The sequences of miRNA may be complementary complimentary to a sequence of target messenger RNA (mRNA) that encodes for translation of a target biomolecule and the miRNA can cause the bioavailability of the target mRNA to decrease because it is degraded or inactivated by the miRNA, thereby causing a decrease in bioactivity of the target biomolecule within a subject that is administered the one or more compositions. In some embodiments of the present disclosure, the target biomolecule is a kinase. In some embodiments of the present disclosure, the target biomolecule is a kinase such as Bruton's tyrosine kinase. In some embodiments of the present disclosure, the target biomolecule is a kinase such as epidermal growth factor (EGF). In some embodiments of the present disclosure, the target biomolecule is a kinase such as vascular endothelial growth factor (VEGF). In some embodiments of the present disclosure, the target biomolecule is a kinase such as B-Raf. In some embodiments of the present disclosure, the target biomolecule is a kinase such as anaplastic lymphoma kinase (ALK). In some embodiments of the present disclosure, the target biomolecule is a kinase such as human epidermal growth factor receptor (HER). In some embodiments of the present disclosure, the target biomolecule is a kinase such as Fms-like tyrosine kinase 3 (FLT3). In some embodiments of the present disclosure, the target biomolecule is a kinase such as poly-ADP ribose polymerase (PARP).

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets mRNA of Bruton's tyrosine kinase.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets mRNA of EGF.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets mRNA of VEGF.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets mRNA of BRAF.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets mRNA of ALK.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets mRNA of HER.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets mRNA of FLT3.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets mRNA of PARP.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, or SEQ ID NO. 9, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence mRNA of a target biomolecule, for example Bruton's tyrosine kinase. A first approach utilizes gene vectors containing nucleotide sequences for increasing the endogenous production of one or more sequences of miRNA, which are complete or partial sequences and/or combinations thereof, that target and silence the mRNA of Bruton's tyrosine kinase, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example EGF. A first approach utilizes gene vectors containing nucleotide sequences for increasing the endogenous production of one or more sequences of miRNA, which are complete or partial sequences and/or combinations thereof, that target and silence the mRNA of EGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example VEGF. A first approach utilizes gene vectors containing nucleotide sequences for increasing the endogenous production of one or more sequences of miRNA, which are complete or partial sequences and/or combinations thereof, that target and silence the mRNA of VEGF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example BRAF. A first approach utilizes gene vectors containing nucleotide sequences for increasing the endogenous production of one or more sequences of miRNA, which are complete or partial sequences and/or combinations thereof, that target and silence the mRNA of BRAF, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example ALK. A first approach utilizes gene vectors containing nucleotide sequences for increasing the endogenous production of one or more sequences of miRNA, which are complete or partial sequences and/or combinations thereof, that target and silence the mRNA of ALK, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example HER. A first approach utilizes gene vectors containing nucleotide sequences for increasing the endogenous production of one or more sequences of miRNA, which are complete or partial sequences and/or combinations thereof, that target and silence the mRNA of HER, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example FLT3. A first approach utilizes gene vectors containing nucleotide sequences for increasing the endogenous production of one or more sequences of miRNA, which are complete or partial sequences and/or combinations thereof, that target and silence the mRNA of FLT3, which can be administered to a subject to increase the subject's production of one or more sequences of the miRNA.

Embodiments of the present disclosure relate to at least one approach for inducing endogenous production of one or more sequences of miRNA that target and silence mRNA of a target biomolecule, for example PARP. A first approach utilizes gene vectors containing nucleotide sequences for increasing the endogenous production of one or more sequences of miRNA, which are complete or partial sequences and/or combinations thereof, that target and silence the mRNA of PARP, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a kinase that is found within a subject. A biomolecule may be endogenous or exogenous to a subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is Bruton's tyrosine kinase.

In some embodiments of the present disclosure, the target biomolecule is EGF.

In some embodiments of the present disclosure, the target biomolecule is VEGF.

In some embodiments of the present disclosure, the target biomolecule is BRAF.

In some embodiments of the present disclosure, the target biomolecule is ALK.

In some embodiments of the present disclosure, the target biomolecule is HER.

In some embodiments of the present disclosure, the target biomolecule is FLT3.

In some embodiments of the present disclosure, the target biomolecule is PARP.

In some embodiments of the present disclosure, the insert comprises one or more nucleotide sequences that each encode one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as Bruton's tyrosine kinase, EGF, VEGF, BRAF, ALK, HER, FLT3, or PARP. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as Bruton's tyrosine kinase, EGF, VEGF, BRAF, ALK, HER, FLT3, or PARP. Increased endogenous expression of the one or more miRNA sequences results in a decreased bioavailability of the desired biomolecule, which may also be referred to as a target biomolecule.

In some embodiments of the present disclosure, the delivery vehicle of the RP used for gene therapy may be a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass. In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adenovirus associated virus (AAV) genome consisting of a RP that when operable inside a target cell will cause the target cell to produce a miRNA sequence that downregulates production of a biomolecule, with examples being Bruton's tyrosine kinase, EGF, VEGF, BRAF, ALK, HER, FLT3, or PARP. The RP is comprised of AAV2 inverted terminal repeats (ITRs), a composite CASI promoter, a human growth hormone (HGH) signal peptide followed by a miRNA expression cassette containing up to six different miRNAs targeting Bruton's tyrosine kinase, EGF, VEGF, BRAF, ALK, HER, FLT3, or PARP, followed by a Woodchuck Hepatitis Virus post-transcriptional regulatory element (WPRE) and an SV40 polyA signal.

SEQ ID NO. 1 (backbone sequence No. 1):
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa -continued

```
tttcacaaataaagcattttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggcttttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaatttttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcaccgtttgaatctttacctacacattactcaggcattgcatttaaaatatatgagggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaaaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca
``` gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgaccccgcccattg acgtcaataatgacgtatgttcccatagtaacgccaatagggactttccattgacgtcaatgggtggagtatttacggtaaactgcccacttgg cagtacatcaagtgtatcatatgccaagtacgcccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttgtgcagcgatggggggggggggggggggggcgcgcgccaggc ggggcggggcggggcgaggggcggggcggggcgaggcggagaggtgcggcggcagccaatcagagcggcgcgctccgaaagttt cctttatggcgaggcggcggcggcggcggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggtttctttccagagagcggaacaggcgaggaaaagtagtcccttctcggcgattctgcggagggatctccgtggg gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgcc

3'

SEQ ID NO. 2 (miRNA expression cassette No. 2 - Bruton's tyrosine kinase):
5' gctagcatcgataccgtcgctatgtgctggaggcttgctgaaggctgtatgctgtaaggtggttatgggagaatgccgttttggcctctgactg acggcattctcctaaccaccttacaggacacaaggcctgttactagcactcacatggaacaaatggcctctagcctggaggcttgctgaagg ctgtatgctgttgagtttcgcattcttgttgccgttttggcctctgactgacggcaacaagagcgaaactcaacaggacacaaggcctgttacta gcactcacatggaacaaatggcctctagcctggaggcttgctgaaggctgtatgctgtctatcctttcaagctagtcaccgttttggcctctgac tgacggtgactagcgaaaggatagacaggacacaaggcctgttactagcactcacatggaacaaatggcctctctagaat

3'

SEQ ID NO. 3 (miRNA expression cassette No. 3 - EGFR):
5' gctagcatcgataccgtcgctatgtgctggaggcttgctgaaggctgtatgctgaagttagcatgtgtcccagaaccgttttggcctctgactg acggttctgggacatgctaacttcaggacacaaggcctgttactagcactcacatggaacaaatggcctctagcctggaggcttgctgaagg ctgtatgctgagaagaaaggtatcccaattgccgttttggcctctgactgacggcaattgggacctttcttctcaggacacaaggcctgttacta gcactcacatggaacaaatggcctctagcctggaggcttgctgaaggctgtatgctgtagtgtttccaaatactgcttgcgttttggcctctgac tgacgcaagcagtatggaaacactacaggacacaaggcctgttactagcactcacatggaacaaatggcctctctagaat

3'

SEQ ID NO. 4 (miRNA expression cassette No. 4 - VEGF):
5' gctagcatcgataccgtcgctatgtgctggaggcttgctgaaggctgtatgctgtctgacagtgatgtcatcctttcgttttggcctctgactgac gaaaggatgatcactgtcagacaggacacaaggcctgttactagcactcacatggaacaaatggcctctagcctggaggcttgctgaaggc tgtatgctgatttaggtcagatggaaactcgcgttttggcctctgactgacgcgagtttccctgacctaaatcaggacacaaggcctgttacta gcactcacatggaacaaatggcctctagcctggaggcttgctgaaggctgtatgctgagtgtatgcttaacgtggacttcgttttggcctctga ctgacgaagtccacgaagcatacactcaggacacaaggcctgttactagcactcacatggaacaaatggcctctctagaat

3'

-continued

SEQ ID NO. 5 (miRNA expression cassette No. 5 - BRAF):
5' gctagcatcgataccgtcgctatgtgctggaggcttgctgaaggctgtatgctgatacttcagcctgaatcgtgaccgttttggcctctgactg acggtcacgattggctgaagtatcaggacacaaggcctgttactagcactcacatggaacaaatggcctctagcctggaggcttgctgaag gctgtatgctgacttcactcatattgttccactcgtttttggcctctgactgacgagtggaacaatgagtgaagtcaggacacaaggcctgttact agcactcacatggaacaaatggcctctagcctggaggcttgctgaaggctgtatgctgtatattctacaaatcaccagggcgttttggcctctg actgacgccctggtgatgtagaatatacaggacacaaggcctgttactagcactcacatggaacaaatggcctctctagaat

3'

SEQ ID NO. 6 (miRNA expression cassette No. 6 - ALK):
5' gctagcatcgataccgtcgctatgtgctggaggcttgctgaaggctgtatgctgtataagtccagtgagaagaaggcgttttggcctctgact gacgccttcttctctggacttatacaggacacaaggcctgttactagcactcacatggaacaaatggcctctagcctggaggcttgctgaagg ctgtatgctgctatcatcaaatgagctgctgcgttttggcctctgactgacgcagcagctcttgatgatagtcaggacacaaggcctgttacta gcactcacatggaacaaatggcctctagcctggaggcttgctgaaggctgtatgctgaagactgctggaaattctatggctgttttggcctctg actgacgaccatagaatccagcagtctcaggacacaaggcctgttactagcactcacatggaacaaatggcctctctagaat

3'

SEQ ID NO. 7 (miRNA expression cassette No. 7 - HER):
5' gctagcatcgataccgtcgctatgtgctggaggcttgctgaaggctgtatgctgattagcactggtgatttccggctgttttggcctctgactga cgaccggaaatccagtgctaatcaggacacaaggcctgttactagcactcacatggaacaaatggcctctagcctggaggcttgctgaagg ctgtatgctgattgagtttcgcattcttgttgccgttttggcctctgactgacggcaacaagagcgaaactcaacaggacacaaggcctgttact agcactcacatggaacaaatggcctctagcctggaggcttgctgaaggctgtatgctgattgatcaggcaaacatagtcccgttttggcctct gactgacgggactatgtgcctgatcaatcaggacacaaggcctgttactagcactcacatggaacaaatggcctctctagaat

3'

SEQ ID NO. 8 (miRNA expression cassette No. 8 - FLT3):
5' gctagcatcgataccgtcgctatgtgctggaggcttgctgaaggctgtatgctgtctgatcgtggtgttatttgggcgttttggcctctgactga cgcccaaataaccacgatcagacaggacacaaggcctgttactagcactcacatggaacaaatggcctctagcctggaggcttgctgaag gctgtatgctgttgagtttcgcattcttgttgccgttttggcctctgactgacggcaacaagagcgaaactcaacaggacacaaggcctgttac tagcactcacatggaacaaatggcctctagcctggaggcttgctgaaggctgtatgctgtatcctcttataactcagcctccgttttggcctctg actgacggaggctgagataagaggatacaggacacaaggcctgttactagcactcacatggaacaaatggcctctctagaat

3'

SEQ ID NO. 9 (miRNA expression cassette No. 9 - PARP):
5' gctagcatcgataccgtcgctatgtgctggaggcttgctgaaggctgtatgctgtcgtactgacttgtaggtatgccgttttggcctctgactga cggcatacctaagtcagtacgtcaggacacaaggcctgttactagcactcacatggaacaaatggcctctagcctggaggcttgctgaagg ctgtatgctgactcctaatcaatagcttccaccgtttttggcctctgactgacggtggaagcttgattaggagtcaggacacaaggcctgttacta gcactcacatggaacaaatggcctctagcctggaggcttgctgaaggctgtatgctgaatatgcctttaagctttgctgcgttttggcctctgac tgacgcagcaaagcaaaggcatattcaggacacaaggcctgttactagcactcacatggaacaaatggcctctctagaat

3'

SEQ ID NO: 10 = SEQ ID NO: 1 + SEQ ID NO: 2
5' aatcaacctctggattacaaaatttgtgaaagattgactggtattcttaactatgttgctcctttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaaccccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggctaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctccctttagggttccgatttagtgctttacggcacctcga ccccaaaaaacttgattagggtgatggttcacgtagtgggccatcgccctgatagacggtttttcgccctttgacgttggagtccacgttctttta atagtggactcttgttccaaactggaacaacactcaaccctatctcggtctattctttgatttataagggattttgccgatttcggcctattggttaa aaaatgagctgatttaacaaaaatttaacgcgaatttttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaattatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaatttttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccogccaacaccogctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccgtagaaaagatcaaaggatcttct -continued tgagatcctttttttctgcgcgtaatctgctgcttgcaaacaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggccttttttacggttcctggccttttgctggccttttgctca catgttcttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatggggcgggggggggggggggcgcgcgccaggc ggggcggggcggggcgagggcggggcggggcgaggcggagaggtgcggcggcagccaatcagagcggcgcgctccgaaagttt ccttttatggcgaggcggcggcggcggcggccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtaaggtggttatgggagaatgccgttttggcctctgactgacggcattctcctaacca ccttacaggacacaaggcctgttactagcactcacatggaacaaatggcctctagcctggaggcttgctgaaggctgtatgctgttgagtttc gcattcttgttgccgttttggcctctgactgacggcaacaagagcgaaactcaacaggacacaaggcctgttactagcactcacatggaaca aatggcctctagcctggaggcttgctgaaggctgtatgctgtctatcctttcaagctagtcaccgtttttggcctctgactgacggtgactagcga aaggatagacaggacacaaggcctgttactagcactcacatggaacaaatggcctctctagaat

3'

SEQ ID NO: 11 = SEQ ID NO: 1 + SEQ ID NO: 3
5' aatcaacctctggattacaaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggcccactccctctctgcgcgctcgct -continued cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattctttttgatttataagggattttgccgatttcggcctattggttaa aaaatgagctgatttaacaaaaatttaacgcgaatttttaacaaaatattaacgtttacaatttaaatatttgcttatacaatcttcctgtttttgggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaattatcagctagaacggttgaatatcatattgatggtgatttgact gtctccggcctttctcacccgtttgaatctttacctacacattactcaggcattgcatttaaaatatatgagggttctaaaaatttttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccagggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga -continued

```
gcgcgcagagagggagtggccaactccatcactagggggttccttgtagttaatgattaacccgccatgctacttatctacgtagccatgctct aggacattgattattgactagtggagttccgcgttacataacttacggtaaatggccgcctggctgaccgcccaacgacccccgcccattg acgtcaataatgacgtatgttcccatagtaacgccaataggggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttatttttttaattatttttgtgcagcgatggggcggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggcccctataaaaagcgaagcgcgcggcgggcgggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgaagttagcatgtgtcccagaaccgttttggcctctgactgacggttctgggacatgct aacttcaggacacaaggcctgttactagcactcacatggaacaaatggcctctagcctggaggcttgctgaaggctgtatgctgagaagaa aggtatcccaattgccgttttggcctctgactgacggcaattgggacctttcttctcaggacacaaggcctgttactagcactcacatggaaca aatggcctctagcctggaggcttgctgaaggctgtatgctgtagtgtttccaaatactgcttgcgttttggcctctgactgacgcaagcagtatg gaaacactacaggacacaaggcctgttactagcactcacatggaacaaatggcctctctagaat

3'

SEQ ID NO: 12 = SEQ ID NO: 1 + SEQ ID NO: 4
5' aatcaacctctggattacaaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacgcgcgaactcatcgccgcctgccttgcccgctgctggacagggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctccctttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgtttttggggct
```

-continued

```
tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacaggtgtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggtttttcaccgtcatcaccgaaacgcgcgagacgaa agggcctcgtgatacgcctattttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgttttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg aagatcctttttgataatctcatgaccaaaatcccttaacgtgagttttcgttccactgagcgtcagacccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctcccacccccaattttgtatttatttattttttaattattttgtgcagcgatggggggggggggggggggggcgcgcgccaggc ggggcggggcggggcgaggggcggggcggggcgaggcggagaggtgcggcggcagccaatcagagcggcgcgctccgaaagttt cctttttatggcgaggcggcggcggcggcggcccctataaaaagcgaagcgcgcggcggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacatttttaggacgggacttgggt
```

```
gactctagggcactggtttttctttccagagagcggaacaggcgaggaaaagtagtcccttctcggcgattctgcggagggatctccgtggg gcggtgaacgccgatgatgcctctactaaccatgttcatgtttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtctgacagtgatgtcatcctttcgttttggcctctgactgacgaaaggatgatcactgt cagacaggacacaaggcctgttactagcactcacatggaacaaatggcctctagcctggaggcttgctgaaggctgtatgctgatttaggtc agatggaaactcgcgttttggcctctgactgacgcgagtttccctgacctaaatcaggacacaaggcctgttactagcactcacatggaacaa atggcctctagcctggaggcttgctgaaggctgtatgctgagtgtatgcttaacgtggacttcgttttggcctctgactgacgaagtccacgaa gcatacactcaggacacaaggcctgttactagcactcacatggaacaaatggcctctctagaat

3'

SEQ ID NO: 13 = SEQ ID NO: 1 + SEQ ID NO: 5
5' aatcaacctctggattacaaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacgcgcgaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtccccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtgtttgtccaaactcatcaatgtatcttatcatgtctggatctcgacctcgactagagc atggctacgtagataagtagcatgggggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaatttaacaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt
```

-continued ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctcccaccccaattttgtatttatttattttttaattattttgtgcagcgatggggggggggggggggggggggcgcgcgccaggc ggggcggggcggggcgaggggcggggcggggcgaggcggagaggtgcggcggcagccaatcagagcggcgcgctccgaaagttt cctttattatggcgaggcggcggcggcggcgggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacatttaggacgggacttgggt gactctagggcactggttttctttccagagagcggaacaggcgaggaaaagtagtcccttctcggcgattctgcggagggatctccgtggg gcggtaacgccgatgatgcctctactaaccatgttcatgttttcttttttttttctacaggtcctgggtgacgaacagggtaccgccaccatggc caccggctctcgcacaagcctgctgctggctttcggactgctgtgcctgccttggctccaggagggctccgcgcctagcatcgataccgtc gctatgtgctggaggcttgctgaaggctgtatgctgatacttcagcctgaatcgtgaccgttttggcctctgactgacggtcacgattggctga agtatcaggacacaaggcctgttactagcactcacatggaacaaatggcctctagcctggaggcttgctgaaggctgtatgctgacttcactc atattgttccactcgtttttggcctctgactgacgagtggaacaatgagtgaagtcaggacacaaggcctgttactagcactcacatggaacaa atggcctctagcctggaggcttgctgaaggctgtatgctgtatattctacaaatcaccagggcgttttggcctctgactgacgccctggtgatg tagaatatacaggacacaaggcctgttactagcactcacatggaacaaatggcctctctagaat

3'

-continued

SEQ ID NO: 14 = SEQ ID NO: 1 + SEQ ID NO: 6
5' aatcaacctctggattacaaaatttgtgaaagattgactggtattcttaactatgttgctcctttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacggcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggggggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggctaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctccctttaggggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattctttttgatttataagggattttgccgatttcggcctattggttaa aaaatgagctgatttaacaaaaatttaacgcgaattttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccgtagaaaagatcaaaggatcttct -continued tgagatcctttttttctgcgcgtaatctgctgcttgcaaacaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacgggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcagggggcggagcctatggaaaaacgccagcaacgcggccttttttacggttcctggcctttttgctggccttttgctca catgttcttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaataggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttgtgcagcgatgggggggggggggggggggggcgcgcgccaggc ggggcggggcggggcgagggcggggcggggcgaggcggagaggtgcggcggcagccaatcagagcggcgcgctccgaaagttt cctttatggcgaggcggcggcggcggcggccctataaaaagcgaagcgcgcgggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtataagtccagtgagaagaaggcgttttggcctctgactgacgccttcttctctggact tatacaggacacaaggcctgttactagcactcacatggaacaaatggcctctagcctggaggcttgctgaaggctgtatgctgctatcatcaa atgagctgctgcgtttggcctctgactgacgcagcagctcttgatgatagtcaggacacaaggcctgttactagcactcacatggaacaaat ggcctctagcctggaggcttgctgaaggctgtatgctgaagactgctggaaattctatggctgttttggcctctgactgacgaccatagaatcc agcagtctcaggacacaaggcctgttactagcactcacatggaacaaatggcctctctagaat

3'

SEQ ID NO: 15 = SEQ ID NO: 1 + SEQ ID NO: 7
5' aatcaacctctggattacaaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaaccccactggttggggcattgccaccacctgtcagctcctttccgggactttcgctttccc cctccctattgccacggcggaactcatcgccgcctgccttgcccgctgctggacagggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcatttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct -continued cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttctttta atagtggactcttgttccaaactggaacaacactcaaccctatctcggtctattcttttgatttataagggattttgccgatttcggcctattggttaa aaaatgagctgatttaacaaaaatttaacgcgaatttttaacaaaatattaacgtttacaatttaaatatttgcttatacaatcttcctgtttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaattatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacaccgccaacaccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccccccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcatttttaatttaaaaggatctaggtg aagatcctttttgataatctcatgaccaaaatcccttaacgtgagttttcgttccactgagcgtcagacccccgtagaaaagatcaaaggatcttct tgagatccttttttttctgcgcgtaatctgctgcttgcaaacaaaaaaaccaccgctaccagcggtggtttgtttgccggatcaagagctaccaac tcttttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggccgcctggctgaccgcccaacgacccccgcccattg acgtcaataatgacgtatgttcccatagtaacgccaataagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc ccccccctccccaccccaattttgtatttatttattttttaattattttttgtgcagcgatgggggggggggggggggggggcgcgcgccaggc gggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaaccccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgattagcactggtgattccggctgtttggcctctgactgacgaccggaaatccagtg ctaatcaggacacaaggcctgttactagcactcacatggaacaaatggcctctagcctggaggcttgctgaaggctgtatgctgattgagttt cgcattcttgttgccgtttggcctctgactgacggcaacaagagcgaaactcaacaggacacaaggcctgttactagcactcacatggaac aaatggcctctagcctggaggcttgctgaaggctgtatgctgattgatcaggcaaacatagtcccgtttttggcctctgactgacgggactatgt gcctgatcaatcaggacacaaggcctgttactagcactcacatggaacaaatggcctctctagaat

3'

SEQ ID NO: 16 = SEQ ID NO: 1 + SEQ ID NO: 8
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacgcgcggaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcattttttttcactgcattctagttgtggtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggctcccttttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaatttttaacaaaatattaacgtttacaatttaaatatttgcttatacaatcttcctgttttttggggct -continued

```
tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaattttttatccttgcgttg aaataaaggcttctcccgcaaaagtattacagggtcataatgttttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctattttttataggttaatgtcatgataataatggtttcttagacgtcaggtggcacttttcggggaaatgtgcgcggaa cccctatttgtttattttttctaaatacattcaaatatgtatccgctcatgagacaataaccctgataaatgcttcaataatattgaaaaaggaagagt atgagtattcaacatttccgtgtcgcccttattccctttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccccccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttttaatttaaaaggatctaggtg aagatcctttttgataatctcatgaccaaaatcccttaacgtgagttttcgttccactgagcgtcagacccccgtagaaaagatcaaaggatcttct tgagatcctttttttctgcgcgtaatctgctgcttgcaaacaaaaaaaccaccgctaccagcggtggtttgtttgccggatcaagagctaccaac tctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactagggggttccttgtagttaatgattaacccgccatgctacttatctacgtagccatgctct aggacattgattattgactagtggagttccgcgttacataacttacggtaaatggcccgcctggctgaccgcccaacgaccccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttatttttttaattattttgtgcagcgatggggggggggggggggggggcgcgcgccaggc ggggcggggcggggcgaggggcggggcggggcgaggcggagaggtgcggcggcagccaatcagagcggcgcgctccgaaagttt cctttatggcgaggcggcggcggcggcggccctataaaaagcgaagcgcgcggcgggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccccagtatcagcagaaggacattttaggacgggacttgggt
```

-continued gactctagggcactggttttctttccagagagcggaacaggcgaggaaaagtagtcccttctcggcgattctgcggagggatctccgtggg gcggtgaacgccgatgatgcctctactaaccatgttcatgtttttcttttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtctgatcgtggtgttatttgggcgtttggcctctgactgacgcccaaataaccacgat cagacaggacacaaggcctgttactagcactcacatggaacaaatggcctctagcctggaggcttgctgaaggctgtatgctgttgagtttc gcattcttgttgccgttttggcctctgactgacggcaacaagagcgaaactcaacaggacacaaggcctgttactagcactcacatggaaca aatggcctctagcctggaggcttgctgaaggctgtatgctgtatcctcttataactcagcctccgtttggcctctgactgacggaggctgagat aagaggatacaggacacaaggcctgttactagcactcacatggaacaaatggcctctctagaat

3'

SEQ ID NO: 17 = SEQ ID NO: 1 + SEQ ID NO: 9
5' aatcaacctctggattacaaaatttgtgaaagattgactggtattcttaactatgttgctccttttacgctatgtggatacgctgctttaatgcctttgt atcatgctattgcttcccgtatggctttcattttctcctccttgtataaatcctggttgctgtctctttatgaggagttgtggcccgttgtcaggcaac gtggcgtggtgtgcactgtgtttgctgacgcaacccccactggttggggcattgccaccacctgtcagctcctttccgggactttcgctttccc cctccctattgccacgcgcgaactcatcgccgcctgccttgcccgctgctggacaggggctcggctgttgggcactgacaattccgtggtgt tgtcggggaaatcatcgtcctttccttggctgctcgcctgtgttgccacctggattctgcgcgggacgtccttctgctacgtcccttcggccctc aatccagcggaccttccttcccgcggcctgctgccggctctgcgggcctcttccgcgtcttcgccttcgccctcagacgagtcggatctcccttt gggccgcctccccgcctaagcttatcgataccgtcgagatctaacttgtttattgcagcttataatggttacaaataaagcaatagcatcacaaa tttcacaaataaagcattttttttcactgcattctagttgtgtttgtccaaactcatcaatgtatcttatcatgtctggatctcgacctcgactagagc atggctacgtagataagtagcatggcgggttaatcattaactacaaggaacccctagtgatggagttggccactccctctctgcgcgctcgct cgctcactgaggccgggcgaccaaaggtcgcccgacgcccgggctttgcccgggcggcctcagtgagcgagcgagcgcgcagctgg cgtaatagcgaagaggcccgcaccgatcgcccttcccaacagttgcgcagcctgaatggcgaatggcgattccgttgcaatggctggcgg taatattgttctggatattaccagcaaggccgatagtttgagttcttctactcaggcaagtgatgttattactaatcaaagaagtattgcgacaac ggttaatttgcgtgatggacagactcttttactcggtggcctcactgattataaaaacacttctcaggattctggcgtaccgttcctgtctaaaatc cctttaatcggcctcctgtttagctcccgctctgattctaacgaggaaagcacgttatacgtgctcgtcaaagcaaccatagtacgcgccctgt agcggcgcattaagcgcggcgggtgtggtggttacgcgcagcgtgaccgctacacttgccagcgccctagcgcccgctcctttcgctttctt cccttcctttctcgccacgttcgccggctttccccgtcaagctctaaatcggggggctcccctttagggttccgatttagtgctttacggcacctcga ccccaaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttgccgatttcggcctattggttaa aaaatgagctgatttaacaaaaatttaacgcgaattttaacaaaatattaacgtttacaatttaaatatttgcttatacaatcttcctgttttttggggct tttctgattatcaaccggggtacatatgattgacatgctagttttacgattaccgttcatcgattctcttgtttgctccagactctcaggcaatgacct gatagcctttgtagagacctctcaaaaatagctaccctctccggcatgaatttatcagctagaacggttgaatatcatattgatggtgatttgact gtctccggcctttctcacccgtttgaatctttacctacacattactcaggcattgcatttaaaatatatgagggttctaaaaatttttatccttgcgttg aaataaaggcttctcccgcaaaagtattacagggtcataatgtttttggtacaaccgatttagctttatgctctgaggctttattgcttaattttgcta attctttgccttgcctgtatgatttattggatgttggaattcctgatgcggtattttctccttacgcatctgtgcggtatttcacaccgcatatggtgca ctctcagtacaatctgctctgatgccgcatagttaagccagccccgacacccgccaacacccgctgacgcgccctgacgggcttgtctgctc ccggcatccgcttacagacaagctgtgaccgtctccgggagctgcatgtgtcagaggttttcaccgtcatcaccgaaacgcgcgagacgaa agggcctcgtgatacgcctatttttataggttaatgtcatgataataatggtttcttagacgtcaggtggcacttttcggggaaatgtgcgcggaa cccctatttgtttatttttctaaatacattcaaatatgtatccgctcatgagacaataacccttgataaatgcttcaataatattgaaaaaggaagagt atgagtattcaacatttccgtgtcgcccttattcccttttttgcggcattttgccttcctgtttttgctcacccagaaacgctggtgaaagtaaaagat gctgaagatcagttgggtgcacgagtgggttacatcgaactggatctcaacagcggtaagatccttgagagttttcgccccgaagaacgtttt ccaatgatgagcacttttaaagttctgctatgtggcgcggtattatcccgtattgacgccgggcaagagcaactcggtcgccgcatacactatt ctcagaatgacttggttgagtactcaccagtcacagaaaagcatcttacggatggcatgacagtaagagaattatgcagtgctgccataacca tgagtgataacactgcggccaacttacttctgacaacgatcggaggaccgaaggagctaaccgctttttttgcacaacatgggggatcatgta actcgccttgatcgttgggaaccggagctgaatgaagccataccaaacgacgagcgtgacaccacgatgcctgtagcaatggcaacaacg ttgcgcaaactattaactggcgaactacttactctagcttcccggcaacaattaatagactggatggaggcggataaagttgcaggaccactt ctgcgctcggcccttccggctggctggtttattgctgataaatctggagccggtgagcgtgggtctcgcggtatcattgcagcactggggcc agatggtaagccctcccgtatcgtagttatctacacgacggggagtcaggcaactatggatgaacgaaatagacagatcgctgagataggt gcctcactgattaagcattggtaactgtcagaccaagtttactcatatatactttagattgatttaaaacttcattttaatttaaaaggatctaggtg aagatcctttttgataatctcatgaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgccggatcaagagctaccaac tcttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagac gatagttaccggataaggcgcagcggtcgggctgaacggggggttcgtgcacacagcccagcttggagcgaacgacctacaccgaact gagatacctacagcgtgagctatgagaaagcgccacgcttcccgaagggagaaaggcggacaggtatccggtaagcggcagggtcgg aacaggagagcgcacgagggagcttccaggggggaaacgcctggtatctttatagtcctgtcgggtttcgccacctctgacttgagcgtcgat ttttgtgatgctcgtcaggggggcggagcctatggaaaaacgccagcaacgcggcctttttacggttcctggccttttgctggccttttgctca catgttctttcctgcgttatcccctgattctgtggataaccgtattaccgcctttgagtgagctgataccgctcgccgcagccgaacgaccgag cgcagcgagtcagtgagcgaggaagcggaagagcgcccaatacgcaaaccgcctctccccgcgcgttggccgattcattaatgcagca gctgcgcgctcgctcgctcactgaggccgcccgggcaaagcccgggcgtcgggcgacctttggtcgcccggcctcagtgagcgagcga gcgcgcagagagggagtggccaactccatcactaggggttccttgtagttaatgattaacccgccatgctacttatctacgtagccatgctct aggacattgattattgactagtggagttccgcgttacataacttacggtaaatggcccgcctggctgaccgcccaacgacccccgcccattg acgtcaataatgacgtatgttcccatagtaacgccaatagggactttccattgacgtcaatgggtggagtatttacggtaaactgcccacttgg cagtacatcaagtgtatcatatgccaagtacgccccctattgacgtcaatgacggtaaatggcccgcctggcattatgcccagtacatgacctt atgggactttcctacttggcagtacatctacgtattagtcatcgctattaccatggtcgaggtgagccccacgttctgcttcactctccccatctc cccccctccccacccccaattttgtatttatttattttttaattattttgtgcagcgatggggggggggggggggggggcgcgcgccaggc ggggcggggcggggcgaggggcggggcggggcgaggcggagaggtgcggcggcagccaatcagagcggcgcgctccgaaagttt ccttttatggcgaggcggcggcggcggcggccctataaaaagcgaagcgcgcggggggggagtcgctgcgcgctgccttcgcccc gtgccccgctccgccgccgcctcgcgccgcccgccccggctctgactgaccgcgttactaaaacaggtaagtccggcctccgcgccggg ttttggcgcctcccgcgggcgcccccctcctcacggcgagcgctgccacgtcagacgaagggcgcagcgagcgtcctgatccttccgcc cggacgctcaggacagcggcccgctgctcataagactcggccttagaacccagtatcagcagaaggacattttaggacgggacttgggt gactctagggcactggttttctttccagagagcggaacaggcgaggaaaagtagtcccttctcggcgattctgcggagggatctccgtggg gcggtgaacgccgatgatgcctctactaaccatgttcatgtttctttttttttctacaggtcctgggtgacgaacagggtaccgccaccatggc caccggctctcgcacaagcctgctgctggctttcggactgctgtgcctgccttggctccaggagggctccgccgctagcatcgataccgtc gctatgtgctggaggcttgctgaaggctgtatgctgtcgtactgacttgtaggtatgccgtttttggcctctgactgacggcatacctaagtcagt acgtcaggacacaaggcctgttactagcactcacatggaacaaatggcctctagcctggaggcttgctgaaggctgtatgctgactcctaat caatagcttccaccgttttggcctctgactgacggtggaagcttgattaggagtcaggacacaaggcctgttactagcactcacatggaacaa atggcctctagcctggaggcttgctgaaggctgtatgctgaatatgcctttaagctttgctgcgttttggcctctgactgacgcagcaaagcaa aggcatattcaggacacaaggcctgttactagcactcacatggaacaaatggcctctctagaat

3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 10-17 or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes are integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) comprising a sequence of nucleotides that is SEQ ID NO: 16.

2. The composition of claim 1, wherein the RP is encapsulated in a protein coat, a lipid vesicle, or any combination thereof.

\* \* \* \* \*